US008920783B2

(12) United States Patent
Lin

(10) Patent No.: US 8,920,783 B2
(45) Date of Patent: *Dec. 30, 2014

(54) SILICONE-ORGANIC ELASTOMER GELS

(75) Inventor: Shaow Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 1115 days.

This patent is subject to a terminal disclaimer.

(21) Appl. No.: 12/293,600

(22) PCT Filed: Mar. 20, 2007

(86) PCT No.: PCT/US2007/006936
§ 371 (c)(1),
(2), (4) Date: Sep. 19, 2008

(87) PCT Pub. No.: WO2007/109282
PCT Pub. Date: Sep. 27, 2007

(65) Prior Publication Data
US 2010/0183525 A1 Jul. 22, 2010

Related U.S. Application Data

(60) Provisional application No. 60/784,340, filed on Mar. 21, 2006, provisional application No. 60/849,397, filed on Oct. 4, 2006, provisional application No. 60/874,203, filed on Dec. 11, 2006.

(51) Int. Cl.
| | | |
|---|---|---|
| *A61K 8/89* | (2006.01) | |
| *A61Q 17/04* | (2006.01) | |
| *A61K 8/31* | (2006.01) | |
| *A61K 8/37* | (2006.01) | |
| *C08G 77/46* | (2006.01) | |
| *A61K 8/58* | (2006.01) | |
| *A61K 8/895* | (2006.01) | |
| *C08G 77/50* | (2006.01) | |
| *C08L 83/04* | (2006.01) | |
| *A61K 8/67* | (2006.01) | |
| *C08L 83/06* | (2006.01) | |
| *A61Q 19/00* | (2006.01) | |
| *A61K 8/04* | (2006.01) | |
| *C08L 83/12* | (2006.01) | |
| *C08G 77/04* | (2006.01) | |
| *C08G 77/20* | (2006.01) | |
| *C08G 77/12* | (2006.01) | |

(52) U.S. Cl.
CPC . *C08L 83/04* (2013.01); *A61K 8/31* (2013.01); *C08G 77/045* (2013.01); *C08G 77/20* (2013.01); *A61K 8/37* (2013.01); *C08G 77/46* (2013.01); *A61K 8/585* (2013.01); *A61K 8/895* (2013.01); *A61Q 17/04* (2013.01); *C08G 77/50* (2013.01); *A61K 8/671* (2013.01); *C08L 83/06* (2013.01); *A61Q 19/00* (2013.01); *C08G 77/12* (2013.01); *A61K 8/042* (2013.01); *C08L 83/12* (2013.01)

USPC .......................................................... 424/59

(58) Field of Classification Search
USPC .......................................................... 424/59
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,296,291 A | 1/1967 | Chalk | |
| 3,419,593 A | 12/1968 | Willing | |
| 3,516,946 A | 6/1970 | Modic | |
| 3,814,730 A | 6/1974 | Karstedt | |
| 3,928,629 A | 12/1975 | Chandra et al. | |
| 3,989,668 A | 11/1976 | Lee et al. | |
| 4,122,029 A | 10/1978 | Gee et al. | |
| 4,987,169 A | 1/1991 | Kuwata et al. | |
| 5,036,117 A | 7/1991 | Chung et al. | |
| 5,171,817 A | 12/1992 | Barnum et al. | |
| 5,175,325 A | 12/1992 | Brown et al. | |
| 5,236,986 A | 8/1993 | Sakuta | |
| 5,380,527 A * | 1/1995 | Legrow et al. ............... 424/401 |
| 5,387,417 A | 2/1995 | Rentsch | |
| 5,412,004 A | 5/1995 | Tachibana et al. | |
| 5,451,637 A | 9/1995 | Leibfried | |
| 5,493,041 A | 2/1996 | Biggs et al. | |
| 5,504,499 A | 4/1996 | Horie et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |

(Continued)

FOREIGN PATENT DOCUMENTS

| | | |
|---|---|---|
| EP | 0848029 | 6/1998 |
| EP | 0922734 | 6/1999 |
| EP | 1069150 | 1/2001 |
| EP | 1148099 | 10/2001 |
| EP | 1266648 | 12/2002 |

(Continued)

OTHER PUBLICATIONS

"Synthesis of New Organic Crosslinking Reagents Containing SiH Bonds and Curing System Thereof" authored by Iwahara et al. and published in Polymer Journal (1993) 25 (4), 379-389.

*Primary Examiner* — Audrea Buckley
(74) *Attorney, Agent, or Firm* — Alan Zombeck

(57) ABSTRACT

Gel compositions are disclosed containing a silicone organic elastomer from the reaction of an organohydrogensiloxane having at least two SiH containing cyclosiloxane rings in its molecule, a compound or mixture of compounds having at least two aliphatic unsaturated groups in its molecule, and a hydrosilylation catalyst. The silicone elastomer reaction product may itself be a gelled composition, or optionally may be contained in a carrier fluid to form a gel. The gel compositions may further contain a personal or healthcare active.

26 Claims, No Drawings

(56) References Cited

U.S. PATENT DOCUMENTS

| | | | |
|---|---|---|---|
| 5,869,727 A * | 2/1999 | Crane et al. | 556/445 |
| 5,880,210 A | 3/1999 | Schulz, Jr. et al. | |
| 5,889,108 A | 3/1999 | Zhang | |
| 5,919,441 A | 7/1999 | Mendolia et al. | |
| 5,929,164 A | 7/1999 | Zhang | |
| 5,981,680 A | 11/1999 | Petroff et al. | |
| 5,998,542 A | 12/1999 | Horne et al. | |
| 6,013,682 A | 1/2000 | Dalle et al. | |
| 6,051,216 A | 4/2000 | Barr et al. | |
| 6,200,581 B1 | 3/2001 | Lin et al. | |
| 6,207,717 B1 | 3/2001 | Lin et al. | |
| 6,262,170 B1 | 7/2001 | Kilgour et al. | |
| 6,271,295 B1 | 8/2001 | Powell et al. | |
| 6,291,563 B1 | 9/2001 | Horne et al. | |
| 6,331,604 B1 | 12/2001 | Wang et al. | |
| 6,365,670 B1 | 4/2002 | Fry | |
| 6,531,540 B1 | 3/2003 | O'Brien | |
| 6,605,734 B2 | 8/2003 | Roy et al. | |
| 7,078,026 B2 | 7/2006 | Ferrari et al. | |
| 2001/0041771 A1 | 11/2001 | Kondon et al. | |
| 2003/0072730 A1 | 4/2003 | Tournilhac | |
| 2003/0170188 A1 | 9/2003 | Ferrari et al. | |
| 2003/0235553 A1 | 12/2003 | Lu et al. | |
| 2004/0091440 A1 * | 5/2004 | Kamei et al. | 424/70.12 |
| 2004/0092655 A1 | 5/2004 | Otomo | |
| 2004/0180032 A1 | 9/2004 | Manelski et al. | |
| 2004/0228821 A1 | 11/2004 | Sunkel et al. | |
| 2009/0317343 A1 | 12/2009 | Lin et al. | |
| 2010/0172849 A1 | 7/2010 | Shaow et al. | |
| 2010/0183525 A1 | 7/2010 | Lin | |

FOREIGN PATENT DOCUMENTS

| | | | |
|---|---|---|---|
| EP | 1266653 | 12/2002 | |
| EP | 1057872 | 2/2006 | |
| EP | 1266647 | 5/2007 | |
| JP | 01207354 | 8/1989 | |
| JP | 01230511 | 9/1989 | |
| JP | 06-049347 | 2/1994 | |
| JP | 08289918 | 11/1996 | |
| WO | WO99/13859 | 3/1999 | |
| WO | WO01/14458 | 3/2001 | |
| WO | 03093349 | 11/2003 | |
| WO | WO03/093349 | 11/2003 | |
| WO | WO03/093369 | 11/2003 | |
| WO | WO03/093369 A1 * | 11/2003 | 424/59 |
| WO | WO03/101412 | 12/2003 | |
| WO | WO03/105789 | 12/2003 | |
| WO | WO03/105801 | 12/2003 | |
| WO | WO03/106614 | 12/2003 | |
| WO | WO04/000247 | 12/2003 | |
| WO | 2004018563 | 3/2004 | |
| WO | WO2004/054523 | 7/2004 | |
| WO | WO2004/054524 | 7/2004 | |
| WO | WO2004/060101 | 7/2004 | |
| WO | WO2004/060271 | 7/2004 | |
| WO | WO2004/060276 | 7/2004 | |
| WO | 2004084844 | 10/2004 | |
| WO | WO2004/103323 | 12/2004 | |
| WO | 2005100444 | 10/2005 | |
| WO | WO2007/109240 | 9/2007 | |
| WO | WO2007/109260 | 9/2007 | |
| WO | WO2007/109282 | 9/2007 | |
| WO | WO2008/085360 | 7/2008 | |
| WO | 2009042535 | 4/2009 | |

* cited by examiner

SILICONE-ORGANIC ELASTOMER GELS

CROSS REFERENCE TO RELATED APPLICATIONS

This application is a U.S. national stage filing under 35 U.S.C. §371 of PCT Application No. PCT/US07/006936 filed on Mar. 20, 2006, currently pending, which claims the benefit of U.S. Patent Application Ser. No. 60/784,340 filed on 21 Mar. 2006, U.S. Patent Application Ser. No. 60/849,397 filed on 4 Oct. 2006 and U.S. Patent Application Ser. No. 60/874,203, filed on 11 Dec. 2006, under 35 U.S.C. §119(e).

TECHNICAL FIELD

This invention relates to gel compositions containing a silicone organic elastomer from the reaction of an organohydrogensiloxane having at least two SiH containing cyclosiloxane rings in its molecule, a compound or mixture of compounds having at least two aliphatic unsaturated hydrocarbon groups in its molecule, and a hydrosilylation catalyst. The silicone organic elastomer reaction product may itself be a gelled composition, or optionally may be contained in a carrier fluid to form a gel. The gel compositions may further contain a personal or healthcare active.

BACKGROUND

Silicone elastomers have been used extensively in personal care applications for their unique silky and powdery sensory profile. Most of these elastomers can gel volatile silicones fluids as well as low polarity organic solvents such as isododecane. Representative examples of such silicone elastomers are taught in U.S. Pat. No. 5,880,210, and U.S. Pat. No. 5,760,116. To improve compatibilities of silicone elastomers with various personal care ingredients, alkyls, polyether, amines or other organofunctional groups have been grafted onto the silicone elastomer backbone. Representative of such organofunctional silicone elastomers are taught in U.S. Pat. No. 5,811,487, U.S. Pat. No. 5,880,210, U.S. Pat. No. 6,200,581, U.S. Pat. No. 5,236,986, U.S. Pat. No. 6,331,604, U.S. Pat. No. 6,262,170, U.S. Pat. No. 6,531,540, and U.S. Pat. No. 6,365,670. Many of these silicone elastomers have limited compatibilities with various personal care ingredients, personal care actives and healthcare actives. These elastomers loose thickening and gelling efficiency, and even sensory benefits in the presence of personal care ingredients, personal care actives and healthcare actives. There is a need to further improve compatibilities of silicone elastomers with various personal care ingredients and actives.

However, there is still a need to further improve the efficiency of gelling volatile cosmetic fluids such as volatile silicones by silicone elastomers, and in particular to improve the rheological thickening effects by the addition of silicone elastomers to volatile cosmetic fluids. Furthermore, additional benefits are also sought for gelled compositions, such as improving the clarity of gelled silicone compositions and/ or improved aesthetics upon application on skin.

The present inventors have discovered that silicone elastomers derived from cyclic organohydrogensiloxanes provide gelled compositions efficiently. The resulting gelled compositions also possess additional benefits, such as improved aesthetics and improved compatibilities with personal care ingredients and actives.

SUMMARY

This disclosure relates to a gel composition comprising a silicone organic elastomer from the reaction of;

A) an organohydrogensiloxane having at least two SiH containing cyclosiloxane rings in its molecule
B) a compound or mixture of compounds having at least two aliphatic unsaturated hydrocarbon groups in its molecule,
C) a hydrosilylation catalyst,
and;
D) an optional carrier fluid;
with the proviso that at least 10 weight % of B) is an organic compound.

This disclosure further relates to a process for preparing a silicone organic elastomer gel containing an active comprising:
I) reacting;
  a) an organohydrogencyclosiloxane having at least two SiH units on a siloxane ring,
  B) a compound or mixture of compounds having at least two aliphatic unsaturated hydrocarbon groups in its molecule,
  C) a hydrosilylation catalyst,
    with the proviso that at least 10 weight % of B) is an organic compound to form
  A) an organohydrogensiloxane having at least two SiH containing cyclosiloxane rings in its molecule,
  wherein the molar ratio of the SiH units of component a) to the aliphatic unsaturated groups of component B) ranges from 2/1 to 8/1,
II) further reacting;
  A) the organohydrogensiloxane having at least two SiH containing cyclosiloxane rings in its molecule, with additional quantities of
  B) the compound or mixture of compounds containing at least two aliphatic unsaturated groups in its molecules,
  C) the hydrosilylation catalyst,
in the presence of
  D) an optional carrier fluid, and
  E) a personal care or healthcare active,
to form the silicone organic elastomer gel.

A personal care or healthcare active may be incorporated into the silicone organic elastomer gel by having it be present during the formation of the silicone organic elastomer gel (pre-load method) or admixing it with a formed silicone organic elastomer gel (post-load method).

DETAILED DESCRIPTION

(A) The Organohydrogensiloxane Having at Least Two SiH Containing Cyclosiloxane Rings Component (A) in the present invention is an organohydrogensiloxane having at least two SiH containing cyclosiloxane rings in its molecule. Organohydrogensiloxanes suitable as component A) in the present invention are any organopolysiloxanes having in its molecule at least two cyclosiloxane rings with at least one silicon bonded hydrogen (SiH) unit on each siloxane ring. Organopolysiloxanes are well known in the art and are often designated as comprising any number of $(R_3SiO_{0.5})$, $(R_2SiO)$, $(RSiO_{1.5})$, or $(SiO_2)$ siloxy units where R is independently any organic group. When R is methyl in the siloxy unit formulas of an organopolysiloxane, the respective siloxy units are often designated as M, D, T or Q siloxy units. Cyclosiloxane rings contain at least three siloxy units (that is the minimum needed in order to form a siloxane ring), and may be any combination of $(R_3SiO_{0.5})$, $(R_2SiO)$, $(RSiO_{1.5})$, or $(SiO_2)$ siloxy units that forms a cyclic structure, providing at least one of the cyclic siloxy units on each siloxane ring contains one SiH unit, that is there is at least one $(R_2HSiO_{0.5})$, $(RHSiO)$, or a $(HSiO_{1.5})$ siloxy unit present in the ring. These siloxy units can be represented as $M^H$, $D^H$, and $T^H$ siloxy units respectively when R is methyl.

The cyclosiloxane rings of A) the organohydrogensiloxane are linked together by a divalent organic or siloxane group, or combination thereof. The divalent linking group may be designated as Y and the cyclosiloxane as G. Thus, the organohydrogensiloxane of the present invention may be represented by the general formula G-[Y-G]$_a$, where G is a cyclosiloxane as described above and Y is a divalent organic, a siloxane, a polyoxyalkylene group, or combination thereof, and the subscript a is greater than zero.

When Y is a divalent organic, it may be a divalent hydrocarbon containing 1 to 30 carbons, either as aliphatic or aromatic structures, and may be branched or un-branched. Alternatively, Y can be an alkylene group containing 2 to 20 carbons, or alternatively containing 4 to 12 carbons.

When Y is a divalent organic, it may also be selected from an organic polymer, such as a polyoxyalkylene group.

When Y is a siloxane group it may be selected from any organopolysiloxane containing at least two divalent hydrocarbon groups, designated as $R^1$. Thus, the siloxane linking group can be any organopolysiloxane comprising at least two siloxane units represented by the average formula $R^1R_m SiO_{(4-m)/2}$ wherein
R is an organic group,
$R^1$ is a divalent hydrocarbon, and
m is zero to 3

The $R^1$ group may be present on any mono, di, or tri-siloxy unit in an organopolysiloxane molecule, for example; $(R^1R_2SiO_{0.5})$, $(R^1RSiO)$, or $(R^1SiO_{1.5})$, as well as in combination with other siloxy units not containing an $R^1$ substituent, such as $(R_3SiO_{0.5})$, $(R_2SiO)$, $(RSiO_{1.5})$, or $(SiO_2)$ siloxy units where R is independently any organic group providing there are at least two $R^1$ substituents in the organopolysiloxane. Representative $R^1$ groups include; ethylene, propylene, butylene, isobutylene, hexylene, and similar homologs. Alternatively, $R^1$ is ethylene.

Representative, non-limiting, examples of such siloxane based structures suitable as siloxane linking groups include;

$(R_2R^1SiO_{0.5})(R_2SiO)_x(R_2R^1SiO_{0.5})$ $(R_3SiO_{0.5})(R_2SiO)_x(R^1RSiO)_y(R_3SiO_{3.5})$ $(R^3SiO_{0.5})(R_2SiO)(R^1RSiO)_y(RSiO_{1.5})_z(R_3SiO_{0.5})$ where x≥0, y≥2, and z is ≥0

Organohydrogensiloxane having at least two SiH containing cyclosiloxane rings (component A) may be prepared via a hydrosilylation reaction of a) an organohydrogencyclosiloxane having at least two SiH units on the siloxane ring and, B) a compound or mixture of compounds having at least two aliphatic unsaturated groups in its molecule.

The organohydrogencyclosiloxane (a) having at least two SiH units on the siloxane ring may contain any number of siloxy units (as defined above) provided there are at least two SiH units on the cyclosiloxane ring. For example, the cyclic siloxane can comprise any number of M, $M^H$, D, $D^H$, or $T^H$ siloxy units. Representative, non-limiting examples of such organohydrogencyclosiloxanes useful to prepare component (A) have the average formula $D^H_aD_b$, where a is ≥1 and b is ≥0, and a+b≥3. Alternatively, the organohydrogencyclosiloxane may be selected from those having the formula $[(CH_3)HSiO]_g$ where g is 3-8, such as $D^H_4$, $D^H_5$, $D^H_6$, or mixtures thereof.

Suitable compounds containing at least two aliphatic unsaturated hydrocarbon groups in its molecule are described below as component B).

Hydrosilylation reactions involving organohydrogensiloxanes and unsaturated compounds are well known. Any suitable hydrosilylation catalysts know in the art may be used, or alternatively may be selected from those described below as component C). Any of the known hydrosilylation techniques and reactions may be employed to prepare component A) from i) organohydrogencyclosiloxane having at least two SiH units on the siloxane ring and, B) a compound or mixture of compounds having at least two aliphatic unsaturated groups in its molecule. However, the reaction is conducted in such a manner to provide an organohydrogensiloxane having at least two SiH containing cyclosiloxane rings in its molecule.

Thus, component A of the present invention contains at least two silicon-bonded hydrogen atom per molecule, alternatively at least 4 silicon-bonded hydrogen atoms per molecule, or alternatively at least 6 silicon-bonded hydrogen atoms per molecule. This can be accomplished by using in the hydrosilylation reaction a molar excess of the a) the organohydrogencyclosiloxane having at least two SiH units on the siloxane ring vs. the compound containing at least two aliphatic unsaturated groups in its molecule. The molar excess may be expressed as the molar ratio of SiH units to unsaturated group, such ratio may range from 2/1 to 8/1, alternatively from 2/1 to 6/1, or alternatively from 3/1 to 4/1.

Alternatively, the organohydrogensiloxane useful as component A) may be selected from any of the organohydrogensiloxanes taught in WO03/093349, which is herein incorporated by reference for its teaching of suitable organohydrogensiloxanes.

The organohydrogensiloxane useful as component A) in the present invention typically have a viscosity from 5 to 50,000 mPa·s, alternatively from 10 to 10,000 mPa·s, or alternatively from 25 to 2,000 mPa·s.

Representative, non-limiting examples of component A) include;

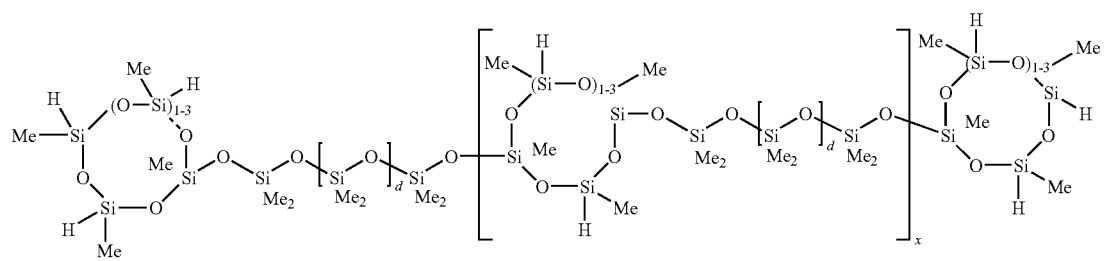

-continued

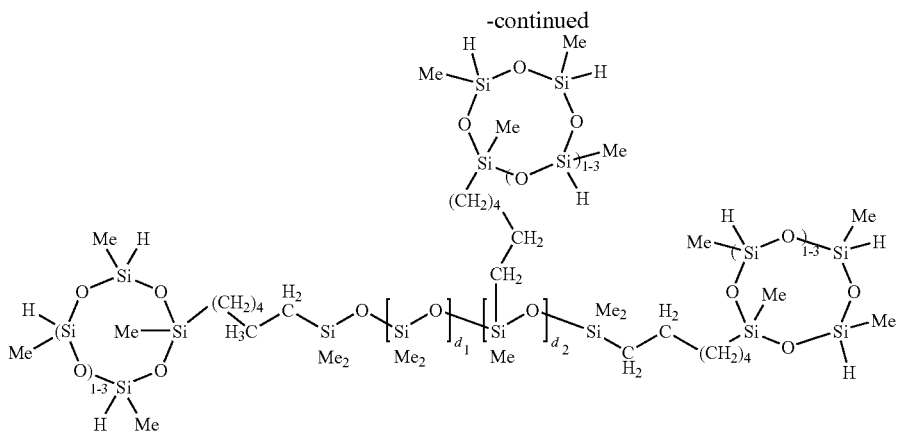

Additives known as inhibitors or stabilizers may be added to component A). Inhibitors such as those described in WO 03/093369 may be added for the purpose of stabilizing component A) during storage, or prior to the addition of component B) to prepare the silicone elastomer gel. The inhibitor may be selected from any compound known to have inhibiting effects of platinum based hydrosilylation reactions. Examples of known inhibitors include triphenyl phosphate, tocopherol (vitamin E), and butylated hydroxy toluene. A particularly preferred inhibitor is vitamin A palmitate, or VAP. When VAP is used, it is typically added at 0.05 to 2.0 parts per 100 parts of component A).

(B) The Compound or Mixture of Compounds Having at Least Two Aliphatic Unsaturated Hydrocarbon Groups in its Molecule Component (B) is a compound, or any mixture of compounds, containing at least two aliphatic unsaturated groups in its molecule. The compound may be any diene, diyne or ene-yne compound. Diene, diyne or ene-yne compounds are those compounds (including polymeric compounds) wherein there are at least two aliphatic unsaturated groups with some separation between the groups within the molecule. Typically, the unsaturation groups are at the termini of the compound, or pendant if part of a polymeric compound. Compounds containing terminal or pendant unsaturated groups can be represented by the formula $R^2$—Y—$R^2$ where $R^2$ is a monovalent unsaturated aliphatic hydrocarbon group containing 2 to 12 carbon atoms, and Y is a divalent organic or siloxane group or a combination of these. Typically $R^2$ is $CH_2=CH-$, $CH_2=CHCH_2-$, $CH_2=CH(CH_2)_4-$, $CH_2=C(CH_3)CH_2-$ or and similar substituted unsaturated groups such as $H_2C=C(CH_3)-$, and $HC\equiv C(CH_3)-$.

The compound having the formula $R^2$—Y—$R^2$ as component B) may be considered as being a "organic", "hydrocarbon", "organic polymer", "polyether" or "siloxane", or combinations thereof, depending on the selection of Y. Y may be a divalent hydrocarbon, a siloxane, a polyoxyalkylene, a polyalkylene, a polyisoalkylene, a hydrocarbon-silicone copolymer, or mixtures thereof.

In one embodiment, the component (B) is selected from an organic compound, herein denoted as ($B^1$), having the formula $R^2$—$Y^1$—$R^2$ where $R^2$ is a monovalent unsaturated aliphatic group containing 2 to 12 carbon atoms and $Y^1$ is a divalent hydrocarbon. The divalent hydrocarbon $Y^1$ may contain 1 to 30 carbons, either as aliphatic or aromatic structures, and may be branched or un-branched. Alternatively, the linking group $Y^1$ in $B^1$ may be an alkylene group containing 1 to 12 carbons. Component ($B^1$) may be selected from α, ω-unsaturated alkenes or alkynes containing 1 to 30 carbons, and mixtures thereof. Component ($B^1$) may be exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

In another embodiment, the component (B) is selected from a $R^2$—$Y^2$—$R^2$ compound where $Y^2$ is a siloxane, herein denoted as ($B^2$). The $Y^2$ siloxane group may be selected from any organopolysiloxane bonded to at least two organic groups having aliphatic unsaturation, designated as $R^2$, to form $R^2$—$Y^2$—$R^2$ structures. Thus, component ($B^2$) can be any organopolysiloxane, and mixtures thereof, comprising at least two siloxane units represented by the average formula $R^2R_mSiO_{(4-m)/2}$
wherein
R is an organic group,
$R^2$ is a monovalent unsaturated aliphatic group as defined above, and
m is zero to 3

The $R^2$ group may be present on any mono, di, or tri siloxy unit in an organopolysiloxane molecule, for example; ($R^2R_2SiO_{0.5}$ ($R^2RSiO$), or ($R^2SiO_{1.5}$); as well as in combination with other siloxy units not containing an $R^2$ substituent, such as ($R_3SiO_{0.5}$ ($R_2SiO$), ($RSiO_{1.5}$), or ($SiO_2$) siloxy units where R is independently any organic group, alternatively a hydrocarbon containing 1 to 30 carbons, alternatively an alkyl group containing 1 to 30 carbons, or alternatively methyl; providing there are at least two $R^2$ substituents in the organopolysiloxane.

Representative, non-limiting, examples of such siloxane based $R^2$—$Y^2$—$R^2$ structures suitable as component ($B^2$) include;

$(R^2R^2SiO_{0.5})(SiO_2)_w(R_2R^2SiO_{0.5})$ $(R_2R^2SiO_{0.5})(SiO_2)_w(R_2SiO)_x(R_2R^2SiO_{0.5})$ $R^2SiO_{0.5})(R_2SiO)_x(R_2R^2SiO_{0.5})$ $(R_3SiO_{0.5})(R_2SiO)_x(R^2RSiO)_y(R_3SiO_{0.5})$ $(R_3SiO_{0.5})(R_2SiO)_x(R^2RSiO)_y(RSiO_{1.5})_z(R_3SiO_{0.5})$ $(R^3SiO_{0.5})(R_2SiO)_x(R^2RSiO)_y(SiO_2)_w(R_3SiO_{0.5})$ where w≥0, x≥0, y≥2, and z is ≥0, R is an organic group, and
$R^2$ is a monovalent unsaturated aliphatic hydrocarbon group.

$B^2$ may be selected from vinyl functional polydimethylsiloxanes (vinyl siloxanes) or hexenyl functional polydimethylsiloxanes (hexenyl siloxanes), such as those having the average formula;

$$CH_2=CH(Me)_2SiO[Me_2SiO]_xSi(Me)_2CH=CH_2$$

$$CH_2=CH-(CH_2)_4-(Me)_2SiO[Me_2SiO]_xSi(Me)_2(CH_2)_4-CH=CH_2$$

$$Me_3SiO[(Me)_2SiO]_x[CH_2=CH(Me)SiO]_ySiMe_3$$

wherein Me is methyl,
x≥0, alternatively x is 0 to 200, alternatively x is 10 to 150,
y≥2, alternatively y is 2 to 50, alternatively y is 2 to 10.
Vinyl functional polydimethylsiloxanes are known, and there are many commercially available.

In another embodiment, component (B) is selected from a polyether compound, herein denoted as ($B^3$), having the formula $R^2$—$Y^3$—$R^2$ compound where $R^2$ is as defined above and $Y^3$ is a polyoxyalkylene group having the formula $(C_nH_{2n}O)_b$ wherein n is from 2 to 4 inclusive, b is greater than 2,
alternatively b can range from 2 to 200,
or alternatively b can range from 2 to 100.

The polyoxyalkylene group typically can comprise oxyethylene units ($C_2H_4O$), oxypropylene units ($C_3H_6O$), oxybutylene or oxytetramethylene units ($C_4H_8O$), or mixtures thereof. Thus, the $R^2$—$Y^3$—$R^2$ compound may be selected from a polyoxyalkylene group having the formula $R^2$—$[(C_2H_4O)_c(C_3H_6O)_d(C_4H_8O)_e]$—$R^2$ where c, d, and e may each independently range from 0 to 200, providing the sum of c+d+e is greater than 2, alternatively the sum of c+d+e ranges from 2 to 200, or alternatively the sum of c+d+e ranges from 2 to 100.

Alternatively, the polyoxyalkylene group comprises only oxypropylene units $(C_3H_6O)_d$. Representative, non-limiting examples of polyoxypropylene containing $R^2$—$Y^3$—$R^2$ compounds include;

$$H_2C=CHCH_2[C_3H_6O]_dCH_2CH=CH_2$$

$$H_2C=CH[C_3H_6O]_dCH=CH_2$$

$$H_2C=C(CH_3)CH_2[C_3H_6O]_dCH_2C(CH_3)=CH_2$$

$$HC\equiv CCH_2[C_3H_6O]_dCH_2C\equiv CH$$

$$HC\equiv CC(CH_3)_2[C_3H_6O]_dC(CH_3)_2C\equiv CH$$

where d is as defined above.
Representative, non-limiting examples of polyoxybutylene or poly(oxytetramethylene) containing $R^2$—$Y^3$—$R^2$ compounds include;

$$H_2C=CHCH_2[C_4H_8O]_eCH_2CH=CH_2$$

$$H_2C=CH[C_4H_8O]_eCH=CH_2$$

$$H_2C=C(CH_3)CH_2[C_4H_8O]_eCH_2C(CH_3)=CH_2$$

$$HC\equiv CCH_2[C_4H_8O]_eCH_2C\equiv CH$$

$$HC\equiv CC(CH_3)_2[C_4H_8O]_eC(CH_3)_2C\equiv CH$$

Component B) may also be a mixture of various polyethers, i.e. a mixture of $B^3$ components.

In another embodiment, component (B) is selected from a $R^2$—$Y^4$—$R^2$ compound, herein denoted as ($B^4$), where $R^2$ is as defined above and $Y^4$ is a polyalkylene group, selected from C2 to C6 alkylene units or their isomers. One example is polyisobutylene group which is a polymer containing isobutylene unit. The molecular weight of the polyisobutylene group may vary, but typically ranges from 100 to 10,000 g/mole. Representative, non-limiting examples of $R^2$—Y—$R^2$ compounds containing a polyisobutylene group includes those obtained from BASF under the tradename of OPPONOL BV, such as OPPONOL BV 5K, a diallyl terminated polyisobutylene having an average molecular weight of 5000 g/mole.

In yet another embodiment, component (B) is selected from a $R^2$—$Y^5$—$R^2$ compound, herein denoted as ($B^5$), where $R^2$ is as defined above and $Y^5$ is a hydrocarbon-silicone copolymer group. The hydrocarbon-silicone copolymer group may have the formula $$-[R^1{}_u(R_2SiO)_v]_q-$$

where $R^1$ and R are as defined above;
u and v are independently ≥1, alternatively u ranges from 1 to 20,
alternatively v ranges from 2 to 500, or from 2 to 200,
q is >1, alternatively q ranges from 2 to 500, alternatively q ranges from 2 to 100.

$R^2$—$Y^5$—$R^2$ compounds having a hydrocarbon-silicone copolymer group may be prepared via a hydrosilylation reaction between an α-ω unsaturated hydrocarbon, such as those described above as $B^1$, and an organohydrogensiloxane. A representative, non-limiting example of such a reaction is shown below.

1,5-Hexadiene    Tetramethyldisiloxane (TMDS)

Component (B) may also be a mixture of any diene, diyne or ene-yne compound, such as any combinations of $B^1$, $B^2$, $B^3$, $B^4$, and $B^5$.

The amounts of component (A) and component (B) used to prepare the present composition will depend on the individual components and the desired SiH to aliphatic unsaturation ratio. The ratio of SiH in component (A) to aliphatic unsaturation from component (B) useful to prepare the compositions of the present invention can be from 10:1 to 1:10, alternatively 5:1 to 1:5, or alternatively 4:1 to 1:4.

If components (A) and (B) are not the only materials containing aliphatic unsaturated groups and SiH-containing groups in the present composition, then the above ratios relate to the total amount of such groups present in the composition rather than only those components.

(C) The Hydrosilylation Catalyst

Component (C) comprises any catalyst typically employed for hydrosilylation reactions. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as $(COD)Pt(SiMeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$.

The appropriate amount of the catalyst will depend upon the particular catalyst used. The platinum catalyst should be present in an amount sufficient to provide at least 2 parts per million (ppm), preferably 4 to 200 ppm of platinum based on total weight percent solids (all non-solvent ingredients) in the composition. It is highly preferred that the platinum is present in an amount sufficient to provide 4 to 150 weight ppm of platinum on the same basis. The catalyst may be added as a single species or as a mixture of two or more different species.

(D) The Carrier Fluid

The silicone elastomers may be contained in an optional carrier fluid (D). Although it is not required, typically the carrier fluid may be the same as the solvent used for conducting the hydrosilylation reaction as described above. Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 $mm^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilypoxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H(C11-C12), hydrogentated polydecen. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME). octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of carrier fluid is such that there is 0 to 98 weight percent, alternatively 0.5 to 90 weight percent, alternatively 5 to 80 weight percent, of carrier fluid in composition containing (A) and (B) and (D), where the sum of (A), (B), and (D) is 100 weight percent.

E) Personal or Healthcare Active

Component E) is active selected from any personal or health care active. As used herein, a "personal care active" means any compound or mixtures of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Thus, active ingredient can include any component that is intended to furnish pharmacological activity or other direct effect in the diagnosis, cure, mitigation, treatment, or prevention of disease, or to affect the structure or any function of the body of a human or other animals. The phrase can include those components that may undergo chemical change in the manufacture of drug products and be present in drug products in a modified form intended to furnish the specified activity or effect.

Some representative examples of active ingredients include; drugs, vitamins, minerals; hormones; topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

Useful active ingredients for use in processes according to the invention include vitamins and its derivatives, including "pro-vitamins". Vitamins useful herein include, but are not limited to, Vitamin $A_1$, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

The active ingredient used in processes according to the invention can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole, clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The active component E) of the present invention can be a protein, such as an enzyme. The internal inclusion of enzymes in the silicone elastomer gel have advantages to prevent enzymes from deactivating and maintain bioactive effects of enzymes for longer time. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said protease include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Said lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

Component E) may also be a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer.

The sunscreen agent can be a single one or combination of more than one. Alternatively, the sunscreen agent is a cinnamate based organic compound, or alternatively, the sunscreen agent is octyl methoxycinnamate, such as Uvinul® MC 80 an ester of para-methoxycinnamic acid and 2-ethylhexanol.

Component E) may also be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these perfume ingredients are described in detail in standard textbook references such as *Perfume and Flavour Chemicals,* 1969, S. Arctander, Montclair, N.J.

Fragrances may be exemplified by, but not limited to, perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-μ-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone, 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-Ionone, Iso-μ-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl) propanal, dihydrocinnamic aldehyde, 1-methyl-4-(4-methyl-3-pentenyl)-3-cyclohexene-1-carboxaldehyde, 5 or 6 methoxyl 0 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for their odor character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

Component E) may also be one or more plant extract. Examples of these components are as follows: Ashitaba extract, avocado extract, hydrangea extract, Althea extract, Arnica extract, aloe extract, apricot extract, apricot kernel extract, *Ginkgo Biloba* extract, fennel extract, turmeric [*Curcuma*] extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, *Pyracantha Fortuneana* Fruit extract, Kiwi extract, Cinchona extract, cucumber extract, guanocine, Gardenia extract, Sasa Albo-marginata extract, Sophora root extract, Walnut extract, Grapefruit extract, Clematis extract, *Chlorella* extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, umbilical cord extract, Salvia extract, *Saponaria* extract, Bamboo extract, *Crataegus* fruit extract, Zanthoxylum fruit extract, shiitake extract, Rehmannia root extract, gromwell extract, *Perilla* extract, linden extract, Filipendula extract, peony extract, Calamus Root extract, white birch extract, Horsetail extract, Hedera Helix(Ivy) extract, hawthorn extract, *Sambucus nigra* extract, *Achillea millefolium* extract, *Mentha piperita* extract, sage extract, mallow extract, *Cnidium officinale* Root extract, Japanese green gentian extract, soybean extract, jujube extract, thyme extract, tea extract, clove extract, *Gramineae imperata* cyrillo extract, *Citrus unshiu* peel extract Japanese *Angellica* Root extract, *Calendula* extract, Peach Kernel extract, Bitter orange peel extract, *Houttuyna cordata* extract, tomato extract, natto extract, Ginseng extract, Green tea extract (*camelliea sinesis*), garlic extract, wild rose extract, hibiscus extract, Ophiopogon tuber extract, *Nelumbo nucifera* extract, parsley extract, honey, hamamelis extract, *Parietaria* extract, *Isodonis herba* extract, bisabolol extract, Loquat extract, coltsfoot extract, butterbur extract, *Porid cocos* wolf extract, extract of butcher's broom, grape extract, propolis extract, *luffa* extract, safflower extract, peppermint extract, linden tree extract, Paeonia extract, hop extract, pine tree extract, horse chestnut extract, Mizu-bashou [*Lysichiton camtschatcese*] extract, Mukurossi peel extract, Melissa extract, peach extract, cornflower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

The amount of component E) present in the silicone gel composition may vary, but typically range as follows;

0.05 to 50 wt %, alternatively 1 to 25 wt %, or alternatively 1 to 10 wt %, based on the amount by weight of silicone elastomer gel present in the composition, that is total weight of components A), B), C) and D) in the silicone gel composition.

The active, component E), may be added to the silicone gel composition either during the making of the silicone elastomer (pre-load method), or added after the formation of the silicone elastomer gel (post load method).

The pre-load method involves;

I) reacting;
  a) an organohydrogencyclosiloxane having at least two SiH units on a siloxane ring,
  B) a compound or mixture of compounds having at least two aliphatic unsaturated hydrocarbon groups in its molecules,
  C) a hydrosilylation catalyst,
    with the proviso that at least 10 weight % of B) is an organic compound, to form
  A) an organohydrogensiloxane having at least two SiH containing cyclosiloxane rings in its molecule,
    wherein the molar ratio of the SiH units of component a) to the aliphatic unsaturated
    hydrocarbon groups of component B) ranges from 2/1 to 8/1,
II) reacting;
  A) the organohydrogensiloxane having at least two SiH containing cyclosiloxane rings in its molecule, with additional quantities of
  B) the compound containing at least two aliphatic unsaturated hydrocarbon groups in its molecules,
  C) the hydrosilylation catalyst,
in the presence of
  D) an optional carrier fluid, and
  E) a personal care or healthcare active,
to form the silicone organic elastomer gel.

The post-load method involves;

I) reacting;
  a) an organohydrogencyclosiloxane having at least two SiH units on a siloxane ring,
  B) a compound or mixture of compounds having at least two aliphatic unsaturated groups in its molecules,
  C) a hydrosilylation catalyst to form
  A) an organohydrogensiloxane having at least two SiH containing cyclosiloxane rings in its molecule,
    wherein the molar ratio of the SiH units of component a) to the aliphatic unsaturated groups of component B) ranges from 2/1 to 8/1,
II) further reacting;
  A) the organohydrogensiloxane having at least two SiH containing cyclosiloxane rings in its molecule, with additional quantities of
  B) the compound containing at least two aliphatic unsaturated groups in its molecules,
  C) the hydrosilylation catalyst,
in the presence of
  D) an optional carrier fluid
to form a silicone elastomer gel,
III) Admixing
  E) a personal care or healthcare active with the silicone elastomer gel to form the silicone elastomer gel containing active.

The Silicone Elastomer

The silicone elastomers of the present invention are obtainable as hydrosilylation reaction products of components A), B), and C). The term "hydrosilylation" means the addition of an organosilicon compound containing silicon-bonded hydrogen, (such as component A) to a compound containing aliphatic unsaturation (such as component B), in the presence of a catalyst (such as component C). Hydrosilylation reactions are known in the art, and any such known methods or techniques may be used to effect the hydrosilylation reaction of components A), B), and C) to prepare the silicone elastomers of the present invention.

The hydrosilylation reaction may be conducted in the presence of a solvent, and the solvent subsequently removed by known techniques. Alternatively, the hydrosilylation may be conducted in a solvent, where the solvent is the same as the carrier fluid described as optional component D).

Alternatively, the silicone elastomers may be prepared by a process comprising:

I) reacting;
  a) an organohydrogencyclosiloxane having at least two SiH units on a siloxane ring,
  B) a compound or mixture of compounds having at least two aliphatic unsaturated hydrocarbon groups in its molecules,
  C) a hydrosilylation catalyst
    with the proviso that at least 10 weight % of B) is an organic compound, to form
  A) an organohydrogensiloxane having at least two SiH containing cyclosiloxane rings in its molecule,
wherein the molar ratio of the SiH units of component a) to the aliphatic unsaturated groups of component B) ranges from 2/1 to 8/1,
  alternatively from 2/1 to 6/1,
    or alternatively from 3/1 to 4/1,
II) further reacting;
  A) the organohydrogensiloxane having at least two SiH containing cyclosiloxane rings in its molecule, with additional quantities of
  B) the compound containing at least two aliphatic unsaturated groups in its molecules,
  C) the hydrosilylation catalyst.
to form a silicone elastomer.

Components a, A), B), C) are the same as those described above. Also, the reaction may be conducted under similar conditions as described above.

In aforementioned step II) the molar ratio of the SiH units of component A) to the aliphatic unsaturated groups of component B) ranges from 10/1 to 1/10,
  alternatively from 5/1 to 1/5,
    or alternatively from 4/1 to 1/4.

Gelled Compositions Containing the Silicone Elastomer

The silicone elastomers can be added to a carrier fluid (as described above as component D) to form gelled compositions, or alternatively be prepared first in a separate reaction and then added to the carrier fluid to obtain a gel. The gelled compositions of the present invention may be characterized by their hardness or firmness. Useful tests to characterize the gels are those recommended by the Gelatin Manufacturers Institute of America such as the use of a "Texture Analyzer" (model TA.XT2, Stable Micro Systems, Inc., Godalming, England). The gel sample is subject to a compression test with the Texture Analyzer having a probe with a 5.0 kg load cell. The probe approaches the surface of the gel at a speed of 0.5 mm/sec and continues compression into the gel to a distance of 5.0 mm, then holds for 1 second before retreating. The Texture Analyzer detects the resistance force the probe experiences during the compression test. The force exhibited by the load cell is plotted as a function of time.

The hardness of the silicone elastomers, gels and elastomer blends (SEBs) for purposes of this invention is defined as the resistance force detected by the probe of the "Texture Analyzer" during the compression test. Two data may used to characterize hardness: Force 1, the force at the maximum compression point (i.e. the 5.0 mm compression point into the gel surface), and Area F-T: the area-force integration during the 1 second hold at the maximum compression point. The average of a total of 5 tests are typically performed for each gel.

The value obtained for Force 1 is converted into Newton (N), by dividing the gram force value by 101.97. (i.e. 1 Newton equals 101.97 g force based on the size of the probe used in this instrument). The second property reported by Texture Analyzer measurement is Area F-T 1:2, in g force·sec. This is the area integration of the force vs. test time cure. This property is indicative of a gel network since it indicates ability to sustain resistance to the compression force, which is relevant to elastomers and gels. The value is reported in g force·sec, and is converted to Newton·sec in SI unit by dividing the value in g force·sec by 101.97.

The silicone gels of the present invention has a compression hardness of at least 200 Newton/m$^2$, alternatively 400 Newton/m$^2$, or alternatively 600 Newton/m$^2$.

Gel Paste Compositions Containing the Silicone Elastomer

The gelled compositions of the present invention can be used to prepare gel paste or gel blend compositions containing actives by;

I) shearing the silicone elastomer gel, as described above,
II) combining the sheared silicone elastomer gel with additional quantities of
D) the carrier fluid, as described above, and optionally
E) a personal or health care active to form a gel paste or blend composition.

The silicone elastomer gel compositions of the present invention blends may be considered as discrete crosslinked silicone elastomer gel particles dispersed in carrier fluids. Thus, the silicone elastomer compositions are effective rheological thickeners for lower molecular weight silicone fluids. As such they can be used to prepare useful gel blend compositions, such as "paste" compositions.

To make such silicone elastomer blends, the aforementioned silicone elastomer gels of known initial elastomer content (IEC) are sheared to obtain small particle size and further diluted to a final elastomer content (FEC). "Shearing", as used herein refers to any shear mixing process, such as obtained from homogenizing, sonalating, or any other mixing processes known in the art as shear mixing. The shear mixing of the silicone elastomer gel composition results in a composition having reduced particle size. The subsequent composition having reduced particle size is then further combined with D) the carrier fluid. The carrier fluid may be any carrier fluid as described above, but typically is a volatile methyl siloxane, such as D5. The technique for combining the D) the carrier fluid with the silicone elastomer composition having reduced particle size is not critical, and typically involves simple stirring or mixing. The resulting compositions may be considered as a paste, having a viscosity greater than 100,000 cP (mPa·s).

EXAMPLES

These examples are intended to illustrate the invention to one of ordinary skill in the art and are should not be interpreted as limiting the scope of the invention set forth in the claims.

Materials Description

The following materials were used in these examples.

Organohydrogensiloxanes

MeH CYCLICS=methylhydrogen cyclosiloxanes (MeH cyclics) having the formula [(CH$_3$)HSiO]$_x$ where the average value of x is 4.4.

Component B) Compounds Containing at Least Two Aliphatic Unsaturated Groups in its Molecule VINYL SILOXANE #1=a dimethylvinylsiloxy-terminated dimethylpolysiloxane of the general formula (CH$_2$=CH)(CH$_3$)$_2$SiO[(CH$_3$)$_2$SiO]$_{dp}$Si(CH$_3$)$_2$(CH=CH$_2$), where the average degree of polymerization (dp) was 8 and having a viscosity of 4 mm$^2$/s at 25° C.

VINYL SILOXANE #2=a dimethylvinylsiloxy-terminated dimethylpolysiloxane of the general formula (CH$_2$=CH)(CH$_3$)$_2$SiO[(CH$_3$)$_2$SiO]$_{dp}$Si(CH$_3$)$_2$(CH=CH$_2$), where the average degree of polymerization (dp) was 130 and having a viscosity of 325 mm$^2$/s at 25° C.

VINYL SILOXANE #3=[(CH$_2$=CH)(CH$_3$)$_2$SiO[(CH$_3$)$_2$SiO]$_{30}$]$_4$Si

VINYL SILOXANE #4=tetramethyltetravinylcyclotetrasiloxane [(CH$_2$=CH)(CH$_3$)SiO]$_4$ VINYL SILOXANE #5=a dimethylvinylsiloxy-terminated dimethylpolysiloxane of the general formula (CH$_2$=CH)(CH$_3$)$_2$SiO[(CH$_3$)$_2$SiO]$_{dp}$Si(CH$_3$)$_2$(CH=CH$_2$), where the average degree of polymerization (dp) was 27 and having a viscosity of 25 mm$^2$/s at 25° C.

VINYL SILOXANE #6=a dimethylhexenylsiloxy-terminated dimethylpolysiloxane of the general formula (CH$_2$=CH(CH$_2$)$_4$)(CH$_3$)$_2$SiO[(CH$_3$)$_2$SiO]$_{dp}$Si(CH$_3$)$_2$((CH$_2$)$_4$(CH$_2$=CH)), where the average degree of polymerization (dp) was 37 and a viscosity of 40 mm$^2$/s at 25° C.

VINYL SILOXANE #7=a dimethylhexenylsiloxy-terminated dimethylpolysiloxane of the general formula (CH$_2$=CH(CH$_2$)$_4$)(CH$_3$)$_2$SiO[(CH$_3$)$_2$SiO]$_{dp}$Si(CH$_3$)$_2$((CH$_2$)$_4$(CH$_2$=CH)), where the average degree of polymerization (dp) was 100 and a viscosity of 170 mm$^2$/s at 25° C.

VINYL SILOXANE #8=a dimethylhexenylsiloxy-terminated dimethylpolysiloxane of the general formula (CH$_2$=CH(CH$_2$)$_4$)(CH$_3$)$_2$SiO[(CH$_3$)$_2$SiO]$_{dp}$Si(CH$_3$)$_2$((CH$_2$)$_4$(CH$_2$=CH)), where the average degree of polymerization (dp) was 200 and a viscosity of 730 mm$^2$/s at 25° C.

VINYL SILOXANE #10=a dimethylvinylsiloxy-terminated dimethylpolysiloxane of the general formula (CH$_2$=CH)(CH$_3$)$_2$SiO[(CH$_3$)$_2$SiO]$_{dp}$Si(CH$_3$)$_2$(CH=CH$_2$), where the average degree of polymerization (dp) was 430.

α,ω-DIALLYL-TERMINATED PIB=Opponol™ BV, an α,ω-diallyl-terminated polyisobutylene having an average molecular weight of 5,000 g/mole, used as obtained from BASF (BASF Corp., Ludwingshafen, Germany).

Hydrosilylation Catalyst
PT CATALYST=SLY-OFF 4000 (Dow Corning Corporation, Midland Mich.) Pt catalyst used as provided containing 0.52 weight % Pt.
Carrier Fluids
D5=decamethylcyclopentasiloxane or D5 cyclics, DC245 (Dow Corning Corporation, Midland Mich.) used as provided.
IDNP=isodecyl neopentanoate obtained from ISP (International Specialty Products Co) under the trade name of CERAPHYL SLK.
IDD=ISODODECANE (Permethyl 99A from Presperse Incorporated, Somerset, N.J.)
Stabilizer=Vitamin A palmitate (VAP) and butylated hydroxytoluene (BHT)
Methods of Measuring Viscosity of Silicone Elastomer Blends (SEBs)

The Brookfield Helipath™ Stand, when used with a suitable Brookfield Viscometer fitted with a special T-bar type spindle, will permit viscosity/consistency measurements in centipoise values for materials having characteristics similar to paste, putty, cream, gelatin, or wax.

The viscosity of silicone elastomer blends was determined using a Brookfield Model RVD-II+ Viscometer with Helipath stand (Brookfield Model D) and T-Bar spindles (Brookfield Helipath Spindle Set). All were purchased from Brookfield Engineering Laboratories, Inc. (11 Commerce Boulevard Middleboro, Mass., USA).

A sample size of 100 g in a 4 oz. round jar was required. The following preparation procedure was used before measurement: the sample was de-aired first via centrifuge, then vacuum de-aired for two hours. After de-airing, the sample was conditioned for a minimum of 4 hours@ 25° C. The sample was positioned with T-bar spindle at center. The reading was taken according to the typical procedure for Helipath spindle.

In general, spindle 93 (T-bar spindle C) is used for the less viscous sample, spindle 95 (T-bar spindle E) for the more viscous samples. The standard setting for rpm was 2.5. The spindle speed is maintained at constant 2.5 rpm and spindle was varied to handle samples with significant viscosities.
Measurement of Silicone Elastomer Gel Hardness The hardness (or firmness) of silicone elastomer gels was characterized using a Texture analyzer (model TA.XT2, Stable Micro Systems, Inc., Godalming, England). The Gelatin Manufacturers Institute of America recommends such test methods as a standard procedure.

For silicone gels and elastomer blends, a ½ inch (1.27 cm) diameter cylindrical probe made of DELRIN acetal resin (Dupont) was used for the measurement. The gel sample is subject to the compression test using the probe with the following test cycle: the probe approaches the surface of the gel at a speed of 0.5 mm/sec and continues compression into the gel to a distance of 5.0 mm, then holds for 1 second before retreating. The Texture Analyzer has a 5.0 Kg load cell to detect the resistance force the probe experiences during the compression test. The force exhibited by the load cell is plotted as a function of time.
The hardness of the silicone elastomers, gels and elastomer blends (SEBs) is defined as the resistance force detected by the probe during the compression test. Two data are used for the hardness value: Force 1: the force at the maximum compression point (i.e. the 5.0 mm compression point into the gel surface), and Area F-T: the area-force integration during the 1 second hold at the maximum compression point. A total of 5 tests were performed for each gel and the average of the five tests is reported.

Texture Analyzer used for gel hardness measurement is force in gram, as detected by the transducer. Two values are reported for gel hardness: Force 1, the force in gram registered when the probe reached its pre-programmed full indentation (or compression) in gel sample. The unit for Force 1 reading is gram force.

The value obtained for Force 1 is converted into Newton (N), by dividing the gram force value by 101.97. (i.e. 1 Newton equals 101.97 g force based on the size of the probe used in this instrument). For instance, a value of 6327 g force converts to 62.0 N.

The second property reported by Texture Analyzer measurement is Area F-T 1:2, in g force·sec. This is the area integration of the force vs. test time cure. This is an indicative property of a gel network as it indicates it ability to sustain resistance to the compression force, which is relevant to elastomers and gels.

The value is reported in g force·sec, and is converted to Newton-sec in SI unit by dividing the value in g force·sec by 101.97. For instance, a value of 33.947 g force·sec is 332.9 N·s in SI units.

Example 1

Reference

Preparation of an Organohydrogensiloxane Having at Least Two SiH Containing Cyclosiloxane Rings-Component A)

Organohydrogensiloxanes having at least two SiH containing cyclosiloxane rings and polydimethylsiloxane spacers between cyclosiloxane rings (for example $G[YG]_a$ where Y is polydimethylsiloxane having a degree of polymerization (DP) of 27, 37, and 100. These organohydrogensiloxanes were made by charging MeH CYCLICS, VINYL SILOXANE (as noted), and the corresponding carrier fluid into a reaction flask, mixed to homogeneous. Then the mixture was catalyzed with 3-5 ppm of Pt (Sly-Off 4000 Pt catalyst solution containing 0.52 wt % Pt). The mixture was heated to 50° C. to causing an exothermic hydrosilylation reaction to occur, the temperature was then maintained between 50 and 70° C. for 3 hours. Then, VAP/BHT (vitamin A palmitate and butylated hydroxytoluene) stabilizer was incorporated to the reaction mixture and then cooled to below 40° C.

The specific compositions and resulting properties for the organohydrogensiloxanes polymers are shown in Table 1.

TABLE 1

| Example # | 1A | 1B | 1C |
|---|---|---|---|
| SiH:Vi ratio | 3.42 | 3.42 | 3.415 |
| Vinyl extender type | VINYL SILOXANE #5 | VINYL SILOXANE #6 | VINYL SILOXANE #7 |
| % SIH compound in mixture | 100.0 | 80.0 | 50.0 |
| Carrier fluid type | | D5 Fluid | D5 |
| Wt. % H, theoretical | 0.1939 | 0.1214 | 0.289 |
| Wt. % H, actual | 0.1932 | 0.1252 | |
| Composition | | | |
| MeH CYCLICS, g | 33.06 | 62.20 | 29.58 |
| VINYL SILOXANE #5, g | 166.97 | | |
| VINYL SILOXANE #6, g | | 418.00 | |
| VINYL SILOXANE #7, g | | | 570.5 |
| D5 Fluid | 0.00 | 120.00 | 600.0 |

TABLE 1-continued

| Example # | 1A | 1B | 1C |
|---|---|---|---|
| Sly-Off 4000, g | 0.160 | 0.035 | 0.45 |
| VAP stabilizer (50% in D5 Fluid), g | 0 | 4.8 | 3.0 |
| Total Batch, g | 200.19 | 605.04 | 1203.5 |
| Mixture appearance | Clear viscous | Clear viscous | Clear viscous liquid |
| Mol. wt., g/mole | 78,303 | 78,303 | |

Example 2

Reference

Preparation of a Hydrocarbon/Silicone Copolymer as a Component B)

Silicone hydrocarbons with diallyl functionalities at ends (α, ω-dihexenyl hydrocarbon oligomers) were prepared by reacting 1,5-hexandiene and tetramethylsiloxane (TMDS) according to the composition in Table 2. The reaction is illustrated below.

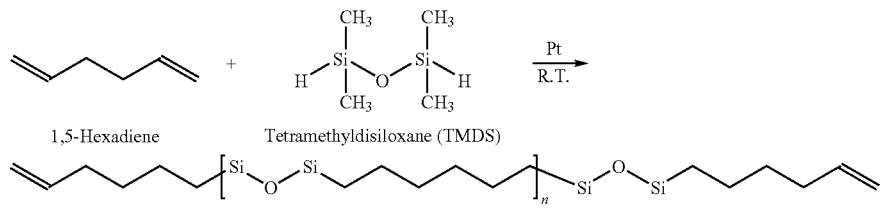

The hexadiene, isododecane or D5 cyclics, and the Pt catalyst were charged to a reactor flask; to which TMDS was added gradually and then the mixture was heated to initiate hydrosilylation reaction. The resulting hydrocarbon/silicone reaction products are summarized in Table 2.

TABLE 2

| Example # | 2A | 2B | 2C |
|---|---|---|---|
| Description | α,ω-C48 diene in Isododecane (41.1% organics) | α,ω-C48 diene in D5 Fluid (41.1% Organics) | α,ω-C24 Oligomeric dienes (44.86% Organics) |
| Diene/TMDS mol. ratio | 8.0/7.0 | 8.0/7.0 | 4.0/3.0 |
| SiH/vinyl equiv. ratio | 0.875 | 0.875 | 0.750 |
| Target MW, g/mole | 1602.4 | 1602.4 | 730.6 |
| % Diene product in the product mixture | 50.0 | 50.0 | 100.0 |
| Wt % Organics in diene | 41.1 | 41.1 | |
| Carrier fluid type | Isododecane | D5 Fluid | |
| Wt % Vinyl in dienes Actual amount | 1.6908 (3.3816 neat) | 1.6908 (33816 neat) | 7.3865 |
| 1,5-Hexadiene, g | 123.50 | 113.04 | 134.67 |
| TMDS, g | 176.70 | 162.50 | 165.33 |
| D5 Fluid, g | | 275.0 | |
| IDD (Permethyl 99A), g | 300.00 | | |

TABLE 2-continued

| Example # | 2A | 2B | 2C |
|---|---|---|---|
| Sly-Off 4000, g (30 drops) | 0.300 | 0.400 | |
| VAP, g (0.5% w/w) | 3.000 | 2.75 | |
| Total Batch, g | 600.5 | 550.94 | 300.246 |
| Mixture appearance | Clear liquid, slightly yellowish tone | Clear liquid, slightly yellowish tone | Clear mixture |

Example 3

Reference

Preparation of a Hydrocarbon/Silicone Copolymer as a Component B)

Hexenyl-terminated silicones of short chain length were prepared as the source of alkenyl-functional compounds for component (B). α,ω-dihexenyl silicones were prepared by reacting 1,5-hexadiene with dimethylhydrogen-terminated silicones M'D$_x$M', where x is the degree of polymerization.

Two examples are summarized in Table 3, using reaction conditions as described above.

TABLE 3

Preparation of α,ω-dihexenyl silicones

| Example # | 3A | 3B |
|---|---|---|
| Description | α,ω-Dihexenyl 15 dp silicones in D5 Fluid; (6.7% Organics) | α,ω-Dihexenyl 30 dp silicones in D5 Fluid; (43% Organics) |
| Diene/TMDS mol. ratio | 3.0/2.0 | 3.0/2.0 |
| SiH/vinyl ratio (equivalent) | 0.667 | 0.667 |
| SiH silicone extender type | 15dp silicone of M'DxM' | 30dp silicone of M'DxM' |
| % Diene product in mixture | 50.0 | 50.0 |
| Wt % Vinyl in extended dienes | 0.7367 (1.473 neat) | 0.471 (0.942 neat) |
| Composition | | |
| 1,5-Hexadiene, g | 10.11 | 6.45 |
| M'DxM' (15dp) silicone, g | 139.97 | |
| 30dp M'DxM' silicone, g | | 143.57 |
| D5 Fluid, g | 150.0 | 150.0 |
| Sly-Off 4000, g (40 drops) | 0.30 | 0.30 |
| Total Batch, g | 300.38 | 300.32 |
| Mixture appearance | Clear mixture, moderate viscosity | Clear mixture, moderate viscosity |

Example 4

Reference

Preparation of an Organohydrogensiloxane Having at Least Two SiH Containing Cyclosiloxane Rings Also Containing Hydrocarbon/Silicone Component as a Component A)

An organohydrogensiloxane having at least two SiH containing cyclosiloxane rings with a desired hydrocarbon-silicone copolymer as spacer was prepared by reacting MeH CYCLICS with α,ω-diallyl hydrocarbon-silicone copolymers of Example 2. The process for the hydrosilylation reaction was similar to those described above using the quantities as described in Table 4.

TABLE 4

| | Example # | | |
|---|---|---|---|
| | 4A | 4B | 4C |
| SiH:Vi ratio | 3.42 | 3.42 | 3.420 |
| Component B) | Hydrocarbon-silicone copolymer from Example 2B | Hydrocarbon-silicone copolymer from Example 2A (50% in IDD) | Hydrocarbon-silicone copolymer from Example 2C |
| Wt % organic in component A) | 28.7 | 32.7 | |
| Carrier fluid type | None | Isododecane | |
| Wt. % H, theoretical | 0.4227 | 0.120 (neat 0.240) | 0.4227 |
| Reaction temp/condition | 40° C. | 70 to 90° C. | |
| Actual amount | | | |
| MeH CYCLICS, g | 72.10 | 25.70 | 72.10 |
| Example 2B C48 diene, g | 127.95 | | |
| Example 2A: C48 diene (50% solids in IDD), g | | 199.90 | |
| Example 2C C24 diene, g | | | 127.95 |
| Isododecane, g | | 25.60 | |
| Sly-Off 4000 Pt, g | 0.120 | 0.090 | 0.240 |
| VAP stabilizer, g | 0.50 | 0.25 | 1.00 |
| Total batch, g | 201.29 | 251.54 | 201.29 |
| Mixture appearance | Clear viscous liquid | Slightly yellowish clear liquid. | Clear viscous mixture |

Example 5

Reference

Preparation of an Organohydrogensiloxane Having at Least Two SiH Containing Cyclosiloxane Rings also Containing Polyisobutylene Organohydrogensiloxanes having at least two SiH containing cyclosiloxane rings with a hydrocarbon spacer based on polyisobutylene (PIB) polymer were prepared by reacting an α,ω-diallyl polyisobutylene of selected molecular weight with SiH functional groups of MeH CYCLICS in the presence of isodecyl neopentanoate (IDNP) solvent. The procedure used was similar to the one used in Example 1. The formulation used and a summary of the properties of the resulting organohydrogensiloxane are summarized in Table 5.

TABLE 5

| | Example # |
|---|---|
| | 5 |
| [SiH]:[Vi] ratio | 3.415 |
| Vinyl extender type | α,ω-DIALLYL-TERMINATED PIB |
| Wt. % H, theoretical | 0.0357 (@ 50% solids) |
| Actual amount | |
| MeH CYCLICS, g | 6.20 |
| α,ω-DIALLYL-TERMINATED PIB, g | 93.95 |
| Isodecyl Neopentanoate, g | 100.4 |
| Sly-Off 4000 Pt, g | 0.080 |
| VAP stabilizer, g | 0.52 |
| Total batch, g | 201.10 |
| Mixture appearance | Hazy, moderate viscosity |

Example 6

Preparation of Silicone Elastomer Gels

Representative silicone elastomer gels were prepared by reacting predetermined amounts of component A), component B), and a Pt catalyst in a carrier fluid (IDD) at 70° C. Clear gels formed within a short period of time at 70° C. The specific composition of these gels is shown in the Table 6.

TABLE 6

| | Example # | | |
|---|---|---|---|
| | 6A | 6B | 6C |
| Organohydrogensiloxane (component (A)) | Example 1B | Example 4B | Example 4B |
| Vinyl extender type (component (B)) | Example #2A and VINYL SILOXANE #2 | Example #2A and VINYL SILOXANE #2 | Example #2A |
| Wt. % Organics in gel | 20.2 | 20.20 | 38.59 |

TABLE 6-continued

|  | Example # | | |
|---|---|---|---|
|  | 6A | 6B | 6C |
| Carrier fluid (component (C)) | IDD | IDD | IDD |
| SiH:Vi ratio | 0.90 | 0.90 | 0.90 |
| % IEC in gel | 20.0 | 20.0 | 20.0 |
| Actual amount | | | |
| Example 1B, g | 29.40 | | |
| Example 4B, g | 0.00 | 24.05 | 39.60 |
| VINYL SILOXANE #2, g | 8.18 | 29.19 | |
| Example #2A, g | 60.60 | 41.60 | 84.43 |
| Isododecane, g | 211.80 | 215.12 | 186.30 |
| Syl-Off 4000 Pt, g | 0.18 | 0.18 | 0.18 |
| Total batch, g | 310.16 | 310.14 | 310.51 |
| Gel appearance | Clear firm gel | Clear firm gel | Clear gel, modeate firmness |

TABLE 6-continued

|  | Example # | | |
|---|---|---|---|
|  | 6A | 6B | 6C |
| Gel hardness, N/m2 | 6,757 | 5,759 | 2,105 |
| Viscosity of gel, N · s/m2 | 37,927 | 31,859 | 12,315 |

The hardness property of these silicone organic elastomer gels was characterized by a Texture Analyzer instrument, as described above.

Example 7

Preparation of Silicone Elastomer Gels

Representative silicone elastomer gels were prepared by reacting predetermined amounts of component A), component B), and a Pt catalyst in a carrier fluid (D5) at 70° C. Clear gels formed within a short period of time at 50° C. The specific composition of these gels is shown in the Table 7.

TABLE 7

Silicone organic elastomer gels in D5 Fluid

|  | Example # | | | |
|---|---|---|---|---|
|  | 7A | 7B | 7C | 7D |
| Component (A) | Example 5C | Example 5C | Example 5C | Example 1A |
| Component (B) | Example 2B | Example 3A | Example 3B | Example 2B |
| Vinyl extender type | | | | |
| Carrier fluid type | D5 Fluid | D5 Fluid | D5 Fluid | D5 Fluid |
| % IEC | 20.0 | 20.0 | 20.0 | 20.0 |
| Composition | | | | |
| Component (A), Example 5C, g | 12.08 | 6.26 | 4.17 | |
| Component (A), Example 1A g | | | | 22.06 |
| Component (B), Example 2B, g | 95.87 | | | 75.89 |
| Component (B), Example 3A g (50% solids) | 0 | 107.51 | | |
| Component (B), Example 3B, g (50% solids) | 0 | | 111.73 | |
| D5 Fluid, g | 192 | 186 | 184.0 | 202 |
| Syl-Off 4000, g | 0.24 | 0.24 | 0.240 | 0.24 |
| Total Batch, g | 300.19 | 300.01 | 300.14 | 300.19 |
| Property | | | | |
| Gel appearance | Clear soft gel | Clear firm gel | Clear firm gel | Clear firm gel |
| Gel hardness (as compression strength), N/m2 | 1,401 | 23,190 | 17,888 | 15,078 |
| Viscosity of gel, N · s/m² or poise (dyne · s/cm2) | 8,336 | 125,190 | 97,155 | 82,394 |

The hardness of the gels were characterized using a Texture Analyzer, as previously described.

Example 8

Preparation of Silicone Elastomer Blends Based on PIB Component

Silicone organic elastomer gels having a high organic content were prepared reacting α,ω-DIALLYL-TERMINATED PIB (Opponol BY 5K Mn, 95 dp) with the organohydrogensiloxanes (from Example 1) in isodecyl neopentanoate were produced, as shown in the Table 8.

TABLE 8

|  | Example # | |
| --- | --- | --- |
|  | 8A | 8B |
| Organohydrogen-siloxane (component (A)) | Example 1B | Example 1C |
| Vinyl extender type (component (B)) | α,ω-DIALLYL-TERMINATED PIB | α,ω-DIALLYL-TERMINATED PIB |
| SiH:Vi ratio | 0.95 | 0.90 |
| % IEC | 20.0 | 20.0 |
| Carrier fluid type | IDNP | IDNP |
| Wt. % Organics in gel | 83.6 | 66.4 |
| Actual amount |  |  |
| Example 1B (80% solids in 245 Fluid), g | 3.30 |  |
| Example 1C (80% solids in 245 Fluid), g |  | 26.47 |
| α,ω-DIALLYL-TERMINATED PIB, g | 26.79 | 26.2 |
| IDNP, g | 50 | 146.92 |
| Syl-Off 4000 Pt, g | 0.08 | 0.12 |
| Total batch, g | 80.17 | 199.71 |
| Gel appearance | Clear, solid gel | Clear gel |
| Gel hardness, N/m2 | 1,819 | 1,293 |
| Viscosity of gel, N · s/m$^2$ | 10,573 | 7,787 |

Example 9

Preparation of Silicone Elastomer Gels Based on PIB Component

Silicone organic elastomer gels having an organic content in the excess of 90% by weight, were prepared using organohydrogensiloxanes from Example 3 as component (A) and α,ω-DIALLYL-TERMINATED PIB polymer (Opponol BV 5K Mn, from BASF Corp., Ludwingshafen, Germany) as component (B). Clear gels in isodecyl neopentanoate were produced. The composition and the property of these high organic elastomer gels are shown in Table 9.

TABLE 9

|  | Example # | |
| --- | --- | --- |
|  | 9A | 9B |
| Organohydrogensiloxane Int. | 2C | 2B |
| Vinyl extender type | α,ω-DIALLYL-TERMINATED PIB | α,ω-DIALLYL-TERMINATED PIB |
| SiH:Vi ratio | 0.95 | 0.95 |
| % IEC | 20.0 | 20.0 |
| Carrier fluid type | IDNP | IDNP |
| Wt. % Organics in gel | 95.1 | 92.7 |

TABLE 9-continued

|  | Example # | |
| --- | --- | --- |
|  | 9A | 9B |
| Actual amount |  |  |
| Example 2C, g | 1.10 |  |
| Example 2B, g |  | 3.57 |
| α,ω-DIALLYL-TERMINATED PIB, g | 30.0 | 28.53 |
| IDNP (Ceraphyl SLK), g | 49.06 | 48.1 |
| Syl-Off 4000, g | 0.08 | 0.08 |
| Total Batch, g | 80.24 | 80.28 |
| Gel appearance | Clear solid gel | Clear, soft gel |
| Gel hardness, N/m2 | 1,262 | 271 |
| Viscosity of gel, N · s/m$^2$ | 7,516 | 1,997 |

Example 10

Preparation of Silicone Elastomer Blends

Silicone organic elastomer blends (SOEBs) were prepared from the silicone elastomer gels (from Example 6) according to the compositions shown in Table 10. These elastomer gels contained 20% initial elastomer content (% IEC) in IDD. The silicone elastomer gels from Example 6 were mechanically ground into micron sized particles and diluted with additional solvent to a selected % elastomer content (% EC) using a high shear device (Waring Blender, Waring Laboratory & Science, Torrington, Conn.). A small amount of vinyl-terminated silicone fluid (4-2764 VEB, Dow Corning) was incorporated as scavenger for any residual SiH group. Illustrated in the Table 10 are SOEBs made to 12% EC in IDD.

TABLE 10

|  | Example # | | |
| --- | --- | --- | --- |
|  | 10A | 10B | 10C |
| Silicone elastomer gel used | 6A | 6B | 6C |
| Wt. % Organics in gel | 20.2 | 20.2 | 38.6 |
| Carrier fluid type | IDD | IDD | IDD |
| SEB formulation: |  |  |  |
| Silicone elastomer gel amount, g | 308.6 | 308.7 | 308.5 |
| IDD, g | 264.0 | 262.9 | 212.6 |
| Vinyl siloxane #1, g | 1.05 | 1.06 | 1.13 |
| Total batch, g | 573.59 | 572.66 | 522.17 |
| % Elastomer content | 12.0 | 12.0 | 12.0 |
| Viscosity, cps | 358,056 | 389,056 | 270,444 |

The viscosity of silicone organic elastomer blend was measured in a Brookfield viscometer equipped with a Helipath stand using a T-bar spindle (Brookfield Engineering, Middleboro, Mass.). The samples were conditioned at 25° C. before the measurement.

Example 11

Preparation of Active Pre-Loaded Silicone Organic Elastomer Gels

Actives were incorporated into the reactive mixtures of the silicone organic components by an "in-situ" method or "pre-load" method. The actives were homogeneously dispersed and trapped within the silicone organic elastomer gel matrix.

Examples of silicone organic elastomer gels with vitamin cured in within the gel matrix are summarized in Table 11. Vitamin A palmitate@ 7.15% by weight was incorporated into silicone organic elastomer gels having 6 to 38.6% organic content were prepared by subjecting the reactive mixtures to 50° C. for 4 hrs. The vitamin containing silicone organic elastomer gels were clear homogeneous.

to disperse homogeneously in the elastomer blend. For instance, vitamin A palmitate (VAP) was post added to the elastomer blend 10 A or B based on IDD, as shown in Examples 12A and B. Retinol 50C was also post added to the elastomer blend 10A and 10

B as shown in Examples 12C and D. The silicone organic elastomer blends (SOEBs) containing actives are summarize in Table 12.

TABLE 11

Silicone organic elastomer gels with vitamin cured in-situ

| | Example # | | | |
|---|---|---|---|---|
| | 11A | 11B | 11C | 11D |
| Description | VAP containing Si-organic elastomer gel in D5 Fluid; 38.61% organics; | VAP containing Si-organic elastomer gel in D5 Fluid; 9.0% organics; | VAP containing Si-organic elastomer gel in D5 Fluid; 6.0% organics; | VAP containing Si-organic elastomer gel in D5 Fluid; 26.0% organics; |
| VAP load, wt. % | 7.15 | 7.15 | 7.15 | 7.15 |
| Component A source | Example 4C | Example 4C | Example 4C | Example 1A |
| Component B source; | Example 2B | Example 3A | Example 3B | Example 2B |
| Carrier fluid type | D5 Fluid | D5 Fluid | D5 Fluid | D5 Fluid |
| % IEC | 20.0 | 20.0 | 20.0 | 20.0 |
| Actual amount | | | | |
| Component A Example 5C, g | 13.75 | 6.87 | 4.60 | |
| Component A Example 1A, g | | | | 23.59 |
| Component B Example 2B, g (50% solids) | 92.57 | | | 72.92 |
| Component B Example 3A, g (50% solids) | 0 | 106.30 | | |
| Component B Example 3B, g (50% solids) | 0 | | 110.85 | |
| D5 Fluid, g | 151.4 | 144.5 | 142.2 | 161.2 |
| Syl-Off 4000, g | 0.24 | 0.24 | 0.240 | 0.24 |
| VAP (50% in D5 Fluid), g | 43.0 | 43.0 | 43.0 | 43.0 |
| Batch total, g | 300.96 | 300.90 | 300.89 | 300.94 |
| Property: | | | | |
| Gel appearance | Clear, bright yellow soft gel | Clear, bright yellow firm gel | Clear, bright yellow firm gel | Clear, bright yellow firm gel |
| Gel hardness (as compression strength), N/m2 | 410 | 8,692 | 7,415 | 8,785 |
| Viscosity of gel, N · s/m² or poise (dyne · s/cm2) | 2,910 | 47,881 | 40,930 | 48,337 |

Example 12

Preparation of Actives Containing Silicone Organic Elastomer Blend by Post-Load Method Silicone organic elastomer blends containing personal care actives were prepared from silicone organic elastomer gels of this invention. Representative silicone organic elastomer gels made above were ground into gel particles of desired size mechanically using a high-shear device. Actives were then mixed in, either neat or in a form of solution in cosmetic fluid,

TABLE 12

Vitamin containing silicone organic elastomer blends by post-load method

| | Example # | | | |
|---|---|---|---|---|
| | 12A | 12B | 12C | 12D |
| Composition: | | | | |
| SOEB Example # | 10A | 10B | 10A | 10B |
| SOEB amount, g | 57.0 | 57.0 | 57.0 | 57.0 |

TABLE 12-continued

Vitamin containing silicone organic elastomer blends by post-load method

| | Example # | | | |
|---|---|---|---|---|
| | 12A | 12B | 12C | 12D |
| VAP, g | 3.0 | 3.0 | | |
| Retinol 50C, g | 0.0 | 0.0 | 3.0 | 3.0 |
| Batch total, g | 60.0 | 60.0 | 60.0 | 60.0 |
| Composition % | | | | |
| Active type | VAP | VAP | Retinol 50C | Retinol 50C |
| % Vitamin | 5.0% | 5.0% | 2.5% | 2.5% |
| % SOEB | 95.0% | 95.0% | 95.0% | 95.0% |
| % Others in vitamin source | | | 2.5% | 2.5% |
| Product appearance | Homogeneous clear paste, with bright yellowish color | Homogeneous clear paste, with bright yellowish color | Light yellowish, hazy paste | Light yellowish, hazy paste |

Example 13

Preparation of Actives Containing Silicone Organic Elastomer Blend by Post-Load Method Examples of vitamin loaded SOEBs in D5 were prepared in a similar manner as described in Example 12 by post-loading vitamin into gels as summarized in Table 13.

TABLE 13

Vitamin containing silicone organic elastomer blend by post-load method

| | Example # | | | |
|---|---|---|---|---|
| | 13A | 13B | 13C | 13D |
| Description | VAP post-loaded into gel | VAP post-loaded into gel | VAP post-loaded into gel | VAP post-loaded into gel |
| Composition | | | | |
| Starting elastomer gel, Example # | 7A | 7B | 7C | 7D |
| Elastomer gel, g | 50.02 | 50.03 | 50.02 | 50.03 |
| D5 Fluid, g | 46.5 | 46.47 | 46.46 | 46.47 |
| VAP active, g | 3.5 | 3.5 | 3.5 | 3.5 |
| Batch total, g | 100.02 | 100.0 | 99.98 | 100.0 |
| Property: | | | | |
| VAP % in SOEB | 3.50 | 3.50 | 3.50 | 3.50 |
| Viscosity, cps | 19,200 | 135,000 | 700,000 | 42,900 |
| Avg gel particle size, μm | 1.0 | 23.4 | 40.1 | 11.9 |

Example 14

Preparation of Vitamin Containing Silicone Organic Elastomer Blends from Pre-Loaded Gels Silicone organic elastomer blend containing vitamins were prepared from silicone organic elastomer gels with vitamin actives homogeneously dispersed/trapped within the gel matrix. The vitamin containing gels were first mechanically ground into small discrete particle sizes, then further diluted with D5 Fluid to desired elastomer content and consistency. Examples of actives containing SOEBs from pre-loaded gels are illustrated in Table 14.

TABLE 14

Vitamin containing silicone organic elastomer blends from pre-loaded gels

| | Example # | | | |
|---|---|---|---|---|
| | 14A | 14B | 14C | 14D |
| Description | VAP pre-loaded into gel | VAP pre-loaded into gel | VAP pre-loaded into gel | VAP pre-loaded into gel |
| Composition | | | | |
| Starting elastomer gel Example # | 11A | 11B | 11C | 11D |
| VAP in starting gel | 7.15 | 7.15 | 7.15 | 7.15 |
| Elastomer gel, g | 50.01 | 50.02 | 50.03 | 50.03 |
| D5 Fluid, g | 50 | 49.98 | 49.97 | 49.97 |
| Batch total, g | 100.01 | 100.0 | 100.0 | 100.0 |
| Property: | | | | |
| VAP % in SOEB | 3.58 | 3.58 | 3.58 | 3.58 |
| Viscosity, cps | 56,400 | 1,040,000 | 1,530,000 | 73,700 |
| Avg gel particle size, um | 1.0 | 47.5 | 40.7 | 35.2 |

Example 15

Preparation of Vitamin Containing Silicone Organic Elastomer Blends from Pre-Loaded Gels Silicone organic elastomer blend containing vitamins were prepared from silicone organic elastomer gels with vitamin actives homogeneously dispersed/trapped within the gel matrix. Silicone organic elastomer gels made in D5 Fluid and in IDNP (isodecyl neopentanoate) organic fluid are shown in this example. Vitamin A palmitate was also incorporated into the silicone organic elastomer gel in-situ. The compositions of these neat and vitamin loaded gels are summarized in the Table 15.

TABLE 15

Neat and vitamin loaded silicone organic gels

| | Example ID | | |
|---|---|---|---|
| | 15A | 15B | 15C |
| Description | Si-Organic gel in D5 fluid; 38.4% organics | Si-Organic gel in IDNP solvent; 38.4% organics | VAP pre-loaded Si-Organic gel in D5 fluid; 38.4% organics |
| Active type and % loading | 0 | 0 | 10% VAP |
| Carrier fluid type | D5 Fluid | IDNP | D5 Fluid |
| Component A Example # | 5A | 5A | 5A |
| Component B Example # | 2B | 2B | 2B |
| % IEC in gel | 20.0 | 20.0 | 20.0 |
| Actual amount | | | |
| Component A, amount, g | 34.82 | 34.83 | 10.62 |
| Component B, amount, g, (50% solids in D5 Fluid) | 81.71 | 81.80 | 20.35 |
| VAP, g | | | 8.02 |
| D5 Fluid | 183.5 | | 41.03 |
| IDNP (Ceraphyl SLK), g | | 183.5 | |

TABLE 15-continued

| Neat and vitamin loaded silicone organic gels | | | |
|---|---|---|---|
| | Example ID | | |
| | 15A | 15B | 15C |
| Syl-Off 4000, g (8 drops) | 0.21 | 0.21 | 0.07 |
| Total Batch, g | 300.24 | 300.34 | 80.09 |
| Property | | | |
| Gel appearance | Clear gel, firm | Clear gel, firm | Clear, yellowish gel, very soft |

Example 16

Silicone Organic Elastomer Blends Containing Vitamins

Examples of silicone organic elastomer blends containing vitamins that were prepared from neat silicone organic gels are illustrated below.

TABLE 16

| Vitamin loaded silicone organic elastomer blends | | |
|---|---|---|
| | Example # | |
| | 16A | 16B |
| SEB Description | VAP post-loaded SOEB in D5 Fluid; 38.4% organics. | VAP post-loaded SOEB in IDNP fluid; 38.4% organics. |
| Active load method | Post-load | Post-load |
| Active type and % loading | 5.0% VAP | 5.0% VAP |
| Carrier fluid type | D5 fluid | IDNP |
| Wt. % Organics in gel | 38.42 | 38.42 |
| Actual amounts into SEB | | |
| Starting gel Example # | 15A | 15B |
| Gel amount, g | 50.00 | 50.09 |

TABLE 16-continued

| Vitamin loaded silicone organic elastomer blends | | |
|---|---|---|
| | Example # | |
| | 16A | 16B |
| D5 Fluid, g | 44.81 | |
| IDNP (Ceraphyl SLK), g | | 44.80 |
| VAP, g | 5.06 | 5.07 |
| Total Batch, g | 100.08 | 100.15 |
| Property: | | |
| Appearance of SEB as made | Slightly yellowish paste | Clear yellow liquid. |
| Viscosity, cps | 90,408 | 1,738 |
| Average gel particle, um | 4.31 | 0.951 |

Example 17

OMC Sunscreen and Vitamin A Containing SOEBs

Other personal care actives may be incorporated into silicone organic elastomer blends described in this invention. Because of the improved compatibility and miscibility over conventional silicone elastomer blends, higher level of organic actives may be incorporated and remain homogeneous and compatible in the elastomer blends.

2-Ethylhexyl methoxycinnamate, also know as OMC (octyl methoxycinnamate), was obtained from ISP (International Specialty Products) under the Escalol 557 name. Retinol (also vitamin A) is obtained from BASF under the name of Retinol 50C. The Retinol 50C contains about 50% of neat retinol and 50% of polysorbate 20 surfactant. They were used as supplied.

The selected silicone elastomer gels were mechanical ground into small particle sizes and diluted further with IDD carrier fluid. The actives were then incorporated into the gels/carrier fluid blend. The specific composition and the final elastomer blend property are summarized Table 17.

The OMC sunscreen loaded elastomer blends were clear and homogeneous paste, indicative of good mutual compatibility. The Retinol 50C containing elastomer blends was opaque, due to the presence of hydrophilic polysorbate 20 surfactant. All elastomer blends retained their high viscosity and pasty consistency suggesting no loss of thixotropic thickening property of the SOEB in IDD.

TABLE 17

| OMC and Retinol loaded silicone organic elastomer blends | | | | |
|---|---|---|---|---|
| | Example # | | | |
| | 17A | 17B | 17C | 17D |
| Description | 11% EC SOEB in IDD; 9.2% OMC post-loaded | 11% EC SOEB in IDD; 18.3% OMC post-loaded | 12% EC SOEB in IDD 10% Retinol 50C post-loaded | 12% EC SOEB in IDD 20% Retinol 50C post-loaded |
| Active type and % loading | 9.2% OMC | 18.3% OMC | 10% Retinol 50C | 20% Retinol 50C |
| Silicone Organic gel | 6B | 6B | 6A | 6A |
| Wt. % Organics in silicone gel | 20.2 | 20.2 | 20.2 | 20.2 |
| Carrier fluid type | IDD | IDD | IDD | IDD |
| % IEC in starting gel | 20.0 | 20.0 | 20.0 | 20.0 |

TABLE 17-continued

OMC and Retinol loaded silicone organic elastomer blends

| | Example # | | | |
|---|---|---|---|---|
| | 17A | 17B | 17C | 17D |
| SEB formulation: Actual | | | | |
| Silicone organic gel amount, g | 54.1 | 54.1 | 54.1 | 54.0 |
| Permethyl 99A (IDD), g | 35.1 | 26.2 | 27.0 | 18.0 |
| OMC (Escalol 557), g | 9.07 | 18.03 | | |
| Retinol 50C, g | | | 9.12 | 18.02 |
| Total Batch, g | 98.24 | 98.25 | 90.21 | 90.05 |
| Appearance of SEB as made | Clear paste | Clear paste | Opaque, slightly yellowish paste | Opaque slightly yellowish paste |

Example 18

OMC Sunscreen in Silicone Organic Elastomer Blends in D5 Fluid

Volatile silicone fluid such as D5 Fluid is a desirable carrier fluid for best sensory feel. The drawback is its limited compatibility with organic active ingredients. However, it is still possible to use it as a carrier fluid for SOEBs in this invention, as the SOEB is a thickening agent for D5 Fluid. Organic active ingredients may be incorporated into the D5 Fluid based SOEB and remain homogenous. Illustrated in the following are OMC containing SOEBs in D5 Fluid.

The selected silicone organic elastomer gels were mechanical ground into small particle sizes and diluted further with D5 Fluid. OMC sunscreen was then incorporated into the gels/carrier fluid blend. The specific composition and the final elastomer blend property are summarized in Table 18.

TABLE 18

OMC sunscreen post-loaded SOEBs in D5 Fluid

| | Example # | | | |
|---|---|---|---|---|
| | 18A | 18B | 18C | 18D |
| Description | 12% EC SOEB in D5 Fluid; 10% OMC in final | 11% EC SOEB in D5 Fluid; 10% OMC in final | 11% EC SOEB in D5 Fluid; 10% OMC in final | 11% EC SOEB in D5 Fluid; 10% OMC in final |
| Active and % load | 10% OMC | 10% OMC | 10% OMC | 10% OMC |
| Silicone organic elastomer blend used | 7A | 7B | 7C | 7D |
| Wt. % Organics in gel | 38.6 | 9.0 | 6.0 | 26.0 |
| Carrier fluid type | D5 Fluid | D5 Fluid | D5 Fluid | D5 Fluid |
| % IEC | 20.0 | 20.0 | 20.0 | 20.0 |
| SEB formulation: actual | | | | |
| SOEB amount, g | 60.1 | 60.2 | 60.2 | 60.1 |
| D5 Fluid, g | 30.0 | 39.0 | 39.2 | 30.0 |
| OMC, g | 10.10 | 10.08 | 10.04 | 9.99 |
| Total Batch, g | 100.22 | 109.24 | 109.41 | 100.09 |
| Property: | | | | |
| Elastomer blend appearance | Homogenous hazy paste | Homogenous hazy paste | Homogenous hazy paste | Homogenous hazy paste |

The invention claimed is:

1. A gel composition comprising a silicone organic elastomer from the reaction of;
   A) an organohydrogensiloxane prepared by a hydrosilylation reaction of
      a) an organohydrogencyclosiloxane having at least two SiH units on the siloxane ring and,
      B) a compound or mixture of compounds having at least two aliphatic unsaturated hydrocarbon groups in its molecule,
   wherein the molar ratio of SiH units of a) the organohydrogencyclosiloxane to aliphatic unsaturated groups of component B) used in the hydrosilylation reaction ranges from 2/1 to 8/1,
      $B^1$) an $\alpha, \omega$-unsaturated alkene or alkyne containing 1 to 30 carbons,
   C) a hydrosilylation catalyst, and
   D) a carrier fluid,
wherein the gel composition has a compression hardness of at least 200 Newton/m$^2$.

2. The composition of claim 1 further comprising;
   E) a personal care or healthcare active.

3. The composition of claim 1 wherein a) the organohydrogencyclosiloxane having at least two SiH units on the siloxane ring has the formula $[(CH_3)HSiO]_g$ where g is 3-8.

4. The composition of claim 1 wherein B) the compound containing at least two aliphatic unsaturated hydrocarbon groups in its molecule is selected from a compound having the formula $R^2$—Y—$R^2$ where $R^2$ is a monovalent unsaturated aliphatic group containing 2 to 12 carbon atoms and Y is a divalent hydrocarbon, a siloxane, a polyoxyalkylene, a polyalkylene, a polyisoalkylene, a hydrocarbon-silicone copolymer, or mixtures thereof.

5. The composition of claim 1 wherein component B) comprises 1,5 hexadiene.

6. The composition of claim 1 wherein B) the compound containing at least two aliphatic unsaturated hydrocarbon groups is selected from an organopolysiloxane comprising at least two siloxane units having a formula $R^2R_mSiO_{(4-m)/2}$
   wherein
      R is an organic group,
      $R^2$ is a monovalent unsaturated aliphatic hydrocarbon group, and
      m is zero to 3.

7. The composition of claim 6 wherein the organopolysiloxane has the formula

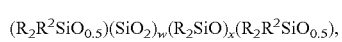

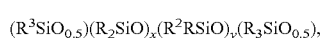

or

where w≥0, x≥0, y≥2, and z is ≥0, R is an organic group, and
$R^2$ is a monovalent unsaturated aliphatic hydrocarbon group.

8. The composition of claim 7 wherein R is methyl and $R^2$ is $CH_2$=CH— or $CH_2$=CH—$(CH_2)_4$—.

9. The composition of claim 7 wherein the organopolysiloxane is a vinyl functional polydimethylsiloxane or hexenyl functional polydimethylsiloxane having the average formula;

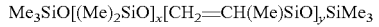
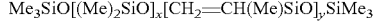

wherein Me is methyl, x≥0, and y≥2.

10. The composition of claim 4 wherein Y in the $R^2$—Y—$R^2$ compound is a hydrocarbon-silicone copolymer group having the formula

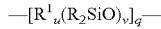

where $R^1$ is a divalent hydrocarbon, R is an organic group, u and v are independently ≥1, and q is >1.

11. The composition of claim 1 wherein
    R is methyl,
    $R^1$ is hexylene,
    u=1, v and q is >1.

12. The composition of claim 11 wherein v ranges from 2 to 500.

13. The composition of claim 11 where q ranges from 2 to 100.

14. The composition of claim 4 wherein Y in the $R^2$—Y—$R^2$ compound is a polyalkylene group.

15. The composition of claim 4 wherein Y in the $R^2$—Y—$R^2$ compound is polyisobutylene.

16. The composition of claim 1 wherein C) the hydrosilylation catalyst is a platinum group containing catalyst.

17. The composition of claim 1 wherein the molar ratio of A)/B) is from 10/1 to 1/10.

18. The composition of claim 1 wherein the carrier fluid is a silicone or organic fluid having a viscosity at 25° C. in the range of 1 to 1,000 mm$^2$/sec.

19. The composition of claim 1 wherein the carrier fluid is decamethylcyclopentasiloxane, isododecane, or isodecyl neopentanoate.

20. The composition of claim 2 wherein E) is a personal care active selected from a vitamin, sunscreen, plant extract, or fragrance.

21. The composition of claim 2 wherein E) is a health care active selected from a topical drug active, protein, enzyme, antifugual, or antimicrobial agent.

22. The composition of claim 2 wherein component E) is vitamin A palmitate.

23. The composition of claim 2 wherein component E) is octyl methoxycinnamate.

24. A process for preparing a gel paste composition comprising;
    I) shearing the silicone elastomer gel of claim 1,
    II) combining the sheared silicone elastomer gel with additional quantities of
       D) the carrier fluid to form a gel paste composition.

25. The process of claim 24 further comprising the addition of
    E) a personal care or healthcare active in step II).

26. The gel paste composition prepared according to the process of claim 24.

* * * * *